United States Patent
Arntsen et al.

(10) Patent No.: US 6,569,911 B1
(45) Date of Patent: May 27, 2003

(54) MANUFACTURING METHOD AND ARTICLE PRODUCED BY THE METHOD

(75) Inventors: Torunn Arntsen, Uppsala (SE); Jan Roger Karlson, Oslo (NO); Geir Fonnum, Rasta (NO); Steinar Hagen, Hagen (NO)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/743,296

(22) PCT Filed: Jul. 13, 1999

(86) PCT No.: PCT/SE99/01261

§ 371 (c)(1),
(2), (4) Date: Mar. 5, 2001

(87) PCT Pub. No.: WO00/03800

PCT Pub. Date: Jan. 27, 2000

(30) Foreign Application Priority Data

Jul. 15, 1998 (GB) .............................................. 9815276

(51) Int. Cl.[7] .......................... C08J 9/36; C08F 132/00; C08F 112/36; C08F 112/34; C08C 19/17

(52) U.S. Cl. .............................. 521/53; 521/30; 521/31; 521/146; 521/149; 521/150; 525/332.1; 525/332.2; 525/370; 525/371; 526/336

(58) Field of Search .............................. 521/53, 30, 31, 521/146, 149, 150; 528/150; 525/332.1, 332.2, 321, 370; 526/336

(56) References Cited

U.S. PATENT DOCUMENTS 5,218,004 A * 6/1993 Meteyer

* cited by examiner

*Primary Examiner*—Morton Foelak
(74) *Attorney, Agent, or Firm*—Royal N. Ronning, Jr.; Stephen G. Ryan

(57) ABSTRACT

A method of manufacturing a support media from a cross-linked polymerisate based on vinyl compounds, and exhibiting residual vinyl groups. The characteristic feature of the method is that the polymerisate is subjected to a heating step that preferably is carried out under reduced access of oxygen. The use of the support media is also described.

11 Claims, No Drawings

MANUFACTURING METHOD AND ARTICLE PRODUCED BY THE METHOD

TECHNICAL FIELD

The invention relates to the manufacture of media that can be used as support in various adsorption processes in order to enrich substances from various liquids, in cell culture, in synthesis taking place on supports and in other fields related to these fields.

The term media refers to the matrix plus the pore volume.

The stationary phase in liquid chromatography is composed of a matrix and is mostly in the form of porous or nonporous particles packed to a bed or in the form of a porous monolith. The matrix should be rigid enough to allow high flow rates without being compressed or broken, for instance when performing separations in columns packed with particles of small diameters. The matrix should also be chemically and physically inert and withstand extreme pH conditions.

In reversed phase chromatography (RPC), particularly for peptide and protein separation, silica gels have for a long time been the preferred stationary phase. These matrices are rigid enough to withstand high flow rates. However, silica gels are not stable above pH 8.0. During recent years there has been a growing interest in synthetic polymeric materials for use in reversed phase high performance liquid chromatography (HPLC), in particular resins based on polymerisation of mono-, di- etc vinyl compounds with particular emphasis of poly vinyl hydrocarbons such as copolymers between styrene and divinylbenzene). These media are often stable with eluents having pH within the range 1–14 and often give excellent separations. The amount of swelling may differ widely depending on fraction of cross-linker to monomer and the liquid they are contacted with. They normally comprise some free unreacted residual vinyl groups (again depending on fraction of cross-linker to monomer) and are not compressed by the pressures normally applied in HPLC.

Polymerisation of vinyl compounds in order to accomplish cross-linked polymerisates/copolymerisates may take place stepwise with a first step resulting in linear non-cross-linked polymers and then in a second step at an increased temperature cross-linking takes place (curing). Often nothing is removed or added between these two steps meaning that for instance significant amounts of initiators and monomers or oligomers with unreacted vinyl groups from the first step remains and are used in the second step. The polymerisate from the first step is characterised by being soft and possible to shape by heating. The second step is often called curing and thus results in a cross-linked copolymerisate. The concept of curing is often utilised in polymerisations, see for instance U.S. Pat. No. 4,977,222; EP 286071 (step e); WPI accession number JP 81-82583D (=JP 56122814) and WPI accession number 81-75832D (DD149672).

WPI accession number 91-257239 (=JP 03168204) describes a cross-linked product from which porogens, monomers, initiators etc are removed in a heating step.
Technical Problem With Prior Art Matrices Based on Polymerised Vinyl Compounds The rigidity of the media is a key issue regarding its ability to withstand high pressures during packing of columns and separations. The packing of media in the form of particles are performed by injecting a suspension of the material into the column with a pressure of several hundred bar. During high performance liquid chromatography (HPLC) the pressure drop over the column can be as high as 200–400 bar.

In order to fulfil these needs a highly cross linked matrix is required. Further, the percentage of polymer matrix in the particle must not be too low. Unfortunately the higher percentage matrix in the media the more the media will swell in an organic solvent.

The ability of media based on vinyl compounds to swell in the presence of organic solvents is one of their major disadvantages when used as the stationary phase in applications requiring flow through the stationary phase, such as in chromatography utilising increased pressure. This becomes particularly troublesome in processes requiring changes in solvents, for instance when solvent gradients are used, such as in reversed phase chromatography (RPC).

OBJECTIVES OF THE INVENTION

A first objective is to provide methods for producing media that are improved concerning the above-mentioned drawbacks.

A second objective is to provide media in which these drawbacks have been reduced.

THE INVENTION

We have now discovered a method for reducing the swelling of vinyl based media without having to change the media composition. Accordingly, one aspect of the invention is a method of manufacturing a media for use as support in the technical field of the invention, preferably in processes requiring contact with organic solvents and optionally with application of liquid pressure. The starting media is a cross linked polymerisate of vinyl compounds, preferably a copolymerisate between a monovinyl compound and a compound exhibiting two or more, preferably two vinyl groups, so that the copolymerisate (media) will exhibit residual vinyl groups. This means that the copolymerisate used in the inventive process is ready-made in the sense that essentially all residual monomers and/or initiators remaining after polymerisation and/or porogens, if present during polymerisation, should have been removed. The characterising feature of the method is that the media (support) is subjected to a heating step, which preferably is carried out at reduced access of oxygen.

The temperature during the heating step should be such that the swellability is decreased. The actual temperature may vary depending on polymer and heating time. A prolonged heating can, for instance, compensate for a lower temperature. It is important not to heat to the extent that a decomposition starts that is harmful to the desired properties of the media. The heating temperature and time thus shall be such that carbonisation does not take place. Normally the temperature is below 500° C. and above 75° C. A representative interval is 120–350° C. with preference in many cases for the interval 180–300° C. These rules particularly apply for matrices based on unsaturated hydrocarbons (vinyl hydrocarbons), such as styrene divinyl benzene.

Reduced access of oxygen means that the heating step may be run under reduced atmospheric pressure or under an inert gas, for instance argon or nitrogen. The main point is that the oxygen pressure is reduced relative to partial oxygen pressure in air at atmospheric pressure. By this term is also contemplated that the matrix is protected from contact with the atmosphere due to being surrounded by a liquid, for instance a hydrocarbon liquid. Particles may for instance be suspended and a monolithic matrix soaked in an inert liquid, such as a hydrocarbon liquid. Often it is advantageous to combine an inert liquid with the application of an inert atmosphere above the liquid, for instance argon or nitrogen.

It has been found that the above-mentioned conditions for the heat treatment may result in matrices exhibiting a reduced back pressure in a packed bed.

It has also been found that it is difficult to prevent oxidation during the heat treatment and that formed oxidised groups have a negative impact on the performance if the media is used in chromatography. It has therefore been found beneficial to post-treat the matrices under conditions providing reduction of oxidised groups formed during the heat treatment. Illustrative reductive agents are for instance those that reduce carbonyl groups, such as in aldehydes and ketones, to alcohol groups or to hydrocarbons. Specifically can be mentioned sodium boro hydride and lithium aluminium hydride. Similar conditions as used elsewhere apply to the respective reductive agent.

The vinyl compound is a compound that exhibits a polymerizable carbon-carbon double bond, such as in vinyl hydrocarbons (vinyl aryls and alkenes), vinyl ethers, acrylates and methacrylates, acrylamides and methacrylamides etc. The term vinyl compound encompasses mono-, di-, tri- etc vinyl compounds. A specifically preferred group of vinyl compounds is the vinyl hydrocarbons, in particular in form of vinyl aryls, for instance various isomers and substituted forms of styrenes and divinyl benzenes. Other examples of vinyl hydrocarbons are buten and 1,3-butadiene. The vinyl compound may contain various substitutes, such as $C_{1-26}$, with particular emphasis of $C_{1-16}$, alkyl groups and functional groups that are compatible with the copolymerisation reaction intended. This has typically been the case for various vinyl benzenes. Copolymerisates of vinyl compounds, in particular between styrenes and divinyl benzenes, have for quite a long time been used as commercially available supports in the field of the invention.

A general property of the media to be used in the present invention is that they swell in contact with an organic solvent, such as methanol, acetonitrile, tetrahydrofuran and other organic solvents used in liquid chromatography. The swelling can be studied, for instance, by measuring the difference of the packed bed volume when going from water to any of the organic liquids just mentioned. Since there always is a desire to minimise this drawback, the invention in principle provides advantages even for media giving an infinitesimal swelling. This latter may be illustrated by the fact that the invention may provide advantages for all media having an increased swelling >0.5% (by volume) when going from water to any of the solvents given above (measured as the volume of a packed bed or a monolithic bed). An better indication of decreased swelling is the lowering in pressure drop found over a bed comprising the matrix in an organic liquid before and after the matrix has been heated in accordance with the invention (packing pressure, applied flow etc all being the same in the comparison).

The number of residual vinyl groups in the polymerisate should typically be within the interval 0.1–5 mmole/g before the thermal treatment start and will typically diminish 1–50% during the heat treatment (measured by bromination). The decrease may differ depending on the specific conditions and methods applied. For instance, treatment at reduced pressure may give a reduction that is lower than treatment in a liquid.

The matrices may be in the form of a porous monolith or in the form of particles that may be porous or non-porous. Porosity may be measured in different ways: surface area per g matrix, pore volume per g matrix and mean pore diameter. The total surface area can be measured by nitrogen adsorption (BET method). The volume of pores with diameters larger than 25 Å can be measured by mercury porosimetry, and smaller pores can be measured by nitrogen desorption.

The selection of matrices having a certain porosity is primarily dependent on the intended use of the media.

For chromatography and other separation purposes it depends on type of chromatography, what to be chromatographed etc. It will also depend on if only diffusive mass transport or diffusive and convective mass transport through the matrix is desired. Diffusive mass transport then normally being satisfied with pore sizes below 1 μm and convective mass transport taking place, mainly in pores larger than 1 μm (flow through pores). For matrices in the form of particles the ratio between pore size and particle diameter normally should be in the range of 0.05–0.5 for flow through pores. Thus the pore size diameter may range from a few Å, such as 50 Å, up to very large values, such as 50 μm. The general condition that the pore diameter always is significantly less than the particle size applies.

The porosity in this field of use typically is: a surface area in the interval 50–1000 m$^2$/g matrix, a pore volume in the interval 0,5 –3 ml/g matrix and a mean pore diameter that may vary from 100–2000 Å.

For porous monoliths the corresponding porosity intervals may be broader, for instance 50 Å–50 μm for pore size diameters.

For cell culture the media may be porous or nonporous. In many cases there will be advantages in case the pores are of such a size and form that they may harbour the cells to be cultured.

As demonstrated in the experimental part, the heat treatment does not need to cause any changes in the porosity.

For particulate matrices the particle size normally is within the range 1–500 μm. Particulate matrices may be monosized (monodispersed) or polysized (polydispersed). By a monosized matrix is typically meant a population of matrix particles having more than 95% of the particles with sizes within mean diameter ±5% of the particles of the population.

After the heat treatment the matrix may be derivatized as well known in the art. For instance by setting the proper hydrophilic/hydrophobic balance on the matrix and/our adding specific binding groups, for instance selected among affinity groups, such as biospecific affinity groups, ion exchange groups (cation or anion exchange groups), amphoteric groups, hydrophobic groups, chelating groups, groups allowing π—π interactions, and groups allowing covalent chromatography. Since one of the largest advantages with the method according the invention is to prepare matrices that can be used together with organic solvents, derivatization often means that a certain degree of hydrophobicity in most cases should be retained. The matrices obtained according to the invention is primarily intended to be used in chromatography utilisutilising organic solvents, with particular emphasis of high pressure liquid chromatography (HPLC). In HPLC the applied pressure is often in the interval 30–300 bar, such as 50–200 bar. One can envisage that the upper limit may go up to 500 bar or even higher. Popular organic solvents are acetonitrile, methanol and tetrahydrofuran. This, however, does not exclude that the matrices also can be used in the connection with aqueous solvents or as support in quite other fields, such as carrier/support in solid phase synthesis, for instance of oligopolypeptides and oligonucleotides, as carrier/support in cell culture etc. The matrices may also be used in other processes involving adsorption from a liquid in which the support functions as the adsorbent (for instance batch-wise processes based on the various affinity groups discussed above).

The invention is further defined in the appended claims and will now be illustrated by the experimental part.

EXPERIMENTAL PART

In our attempt to reduce the shrinking/swelling behaviour and increase the rigidity of reverse phase chromatographic media based on synthetic polymers built up from vinyl monomers we have worked along the following lines: a) base particle development, b) other chemical modifications and c) thermal treatment. The alternative with thermal treatment gave the most promising results and has therefore been developed further. See below.

The media used as a model substance for the study was copolymerisate particles of divinyl-benzene (80%) and ethyl vinyl-benzene (20%). The media was prepared as outlined by Ugelstad (U.S. Pat. No. 4,336,173; U.S. Pat. No. 4,336, 173 and U.S. Pat. No. 4,459,378) and was obtained in form of monosized porous particles of 5 $\mu$m or 15 $\mu$m. The pore characteristics of the 5 $\mu$m particles were: surface area 634m$^2$/g, pore volume: 1.25 ml/g with 1.67 mmole/g of vinyl groups. To remove seed-particles, porogens and possible rests of monomer and initiator the particles were extensively extracted with an organic solvent before further use.

Thermal Treatment (Procedure 1):

The base particles were filtered and dried in an incubator at 50° C. over night. Dry particles (10 g of 5 $\mu$m particles) were placed in a vacuum oven which was evacuated before heating. The time was recorded from the time the temperature had reached the pre-set value. After the predetermined number of heating hours, the heating was turned off and the sample was cooled in vacuum. When the temperature was below 50° C., the vacuum pump was turned off and the sample removed from the oven. The conditions were varied as given in table 1.

Thermal Treatment (Procedure 2):

Dry particles (10 g, 15 $\mu$m particles) were added to hexadecane (100 ml). The mixture was heated at 200° C. for 4 h under inert atmosphere (argon). The mixture was cooled to 50° C., filtered and washed with acetone (600 ml) and methanol (600 ml).

Reductive Treatment:

Dry heat treated media (240° C. for 15 h, 4 g) was added to ethanol (35 ml) and treated with ultrasound for 15 minutes. The slurry was then transferred to a reactor, and ethanol (5 ml) was used for rinsing. Sodium boro hydride (0.025 g) was added. The mixture was stirred at room temperature for 30 min before it was filtered and washed with 20% ethanol (200 ml).

Test for Back Pressure of the Media:

The test was carried out in the following equipment:

| | |
|---|---|
| System: | ÄKTA XT (Amersham Pharmacia Biotech AB, Uppsala, Sweden) |
| Solvent A: | Methanol |
| Solvent B: | Water |
| Flow: | 1.0 ml/min |
| Columns: | 4.6 × 150 mm Jour Research steel columns |
| Packing solutions: | 100% Methanol |
| Packing pressure: | 700 bar |
| Packing time: | 1 hour |
| Slurry concentration: | 15 ml sediment in 25 ml total volume |
| Packing reservoir: | 4.6/250 mm |

Comments: If the media do not swell in methanol, the pressure difference between water and methanol is correlated to the viscosity of the solutions. The viscosity of water at 20° C. is 1.00 cp and of methanol at 20° C. is 0.59 cp. Hence, a media that does not swell will give 41% lower pressure in methanol compared to water. It is important that media which are compared are packed at equal pressures

TABLE 1

| | | Measured pressures | | | |
|---|---|---|---|---|---|
| Media | Treatment[1] | back press. water[2] | back press methanol[3] | Pressure difference[4] | Comments |
| Base part | None | 99 | 127 | 28 | Untreated |
| 1 | 240/15 | 151 | 134 | −11 | Reduced |
| 2 | 240/15 | 162 | 157 | −3 | Oxidised, 2 mbar |
| 3 | 240/15 | 156 | 137 | −12 | |
| 4 | 240/15 | 144 | 118 | −18 | |
| 5 | 250/15 | 146 | 129 | −12 | |
| 6 | 230/15 | 154 | 138 | −10 | |
| 7 | 210/15 | 137 | 138 | 1 | |
| 8 | 240/17 | 158 | 138 | −13 | |
| 9 | 240/13 | 144 | 126 | −13 | |
| 10 | 240/10 | 124 | 107 | −14 | |
| 11 | 240/8 | 143 | 117 | −18 | |
| 12 | 240/15 | 165 | 142 | −14 | |
| 13 | 240115 | 156 | 134 | −14 | |
| 14 | 210/12 | 141 | 134 | −5 | |
| 15 | 210/10 | 137 | 124 | −9 | |
| 16 | 180/15 | 121 | 138 | 14 | |
| 17 | 240/15 | 124 | 103 | −17 | |
| 18 | 180/4 | 131 | 166 | 27 | |
| 19 | 240/4 | 153 | 147 | 4 | batch 1 |
| 20 | 240/4 | 152 | 144 | −5 | batch 2 |
| 21 | 240/4 | 140 | 146 | 4 | batch 3 |

[1]Incubation condition thermal treatment (° C.)/(h)t;
[2]Back pressure in water at 1 ml/min (bar);
[3]Back pressure in methanol at 1 ml/min (bar);
[4]Back pressure difference in % with change from water to methanol Table 1 shows that the back pressure over the column in methanol is 28% higher than in water for the media before thermal treatment. This increase in back pressure is caused by the swelling of the particles in the organic solvent (methanol). After thermal treatment the reduced shrinking behaviour of the media causes the back pressure in methanol to be 10–20% lower than in water.

Other Changes Studied:

A) The thermal treatment caused only minor changes in surface area and pore volume.
B) FT-IR spectra showed changes in the presence of the following type of groups: a) decreased amount of vinyl groups, b) increase in aromatic substitution, possibly due to cross-linking, c) increase in carbonyl groups, probably due to introduction of aldehyde and/or ketone groups.

Effect of Temperature, Time and Pressure Applied During Thermal Treatment (Reduced Pressure):

A) Effect of temperature. The temperature was varied from 180° C. to 250° C. Heating time was 15 hs. A graphical representation of the correlation between shrinking/swelling and temperature showed that the shrinking/swelling characteristics of the media (particles) decrease up to about 230° C., after which it seemed to become stable.

B) Effect of heating time. The heating time was varied in the interval 4–17 h. The temperature was kept constant to 240° C. The results showed that the heating time is of some importance regarding shrinking/swelling. At 240° C. the amount of shrinking/swelling seems to be reduced during the first 8 hours after which no further changes seem to occur.

C) Effect of pressure. The pressure was varied in the interval 0.02–50 mb. The temperature was 240° C. and the heating time was 15 h. No correlation between shrinking/swelling of the media (particles) and pressure could be found. Based on FT-IR it was recognized that the pressure had a large effect on the amount of oxidation, with the main contribution in the interval up to 2 mb.

The optimal conditions for the reduction of shrinking/swelling for this specific media can be found from table 1.

Chromatographic Testing:

This was run as a separation of various mixtures of PTH amino acids, bradykinin peptides and angiotensins.

The outcome was that chromatography of this test mixtures on the heat treated media gave the narrowest peaks compared to media not having undergone the heat treatment. Further, the results showed that matrices in which the heat treatment had introduced oxidised groups gave a poorer chromatographic performance (shorter peak heights and broader peaks due to charge/dipole interactions.

Added During the Priority Year.

It has been recognized that during the heating step according to the invention there may also take place advantageous derivatizing reactions in case the starting copolymerisate is heated in a non-inert liquid or in inert liquid containing reactive entities. Thus for instance:

Heating to 120° C. in decanol with 0.05 M p-toluene sulphonic acid introduces decyl ether groups at either of the carbon atoms in residual vinyl groups. Without presence of p-toluene sulphonic acid no reaction with decanol was detectable.

Heating to 200° C. in $(C_2H_4OH)_2NH$ inserts amino groups.

Heating in the presence of $H_2NC_3H_6O(C_2H_4O)_2$ $C_3H_6NH_2$ also introduces amino groups on the cross-linked copolymerisate.

Thus in a further aspect of the present invention heating is taking place in the presence of a compound exhibiting one or more functional groups at least one of which being reactive with the copolymerisate under the conditions applied thereby covalently linking said compound to said copolymerisate. The compound is typically an organic compound. The heating can take place either with or without immersing the copolymerisate in a liquid that by itself may exhibit reactive functional groups or contain in dissolved form compounds exhibiting such groups. Preferably the heating should take place under reduced access of oxygen as mentioned above. Substances promoting the particular derivatisation contemplated may be present in the medium surrounding the copolymerisate. Thus the heating, whenever found appropriate, may place in the presence of acids or bases.

In this aspect of the invention groups such as amino groups, hydroxy groups, oxyethylene groups, ether groups, hydrocarbon groups etc and other functional groups may be introduced. It follows that this mode of the invention also could be used for hydrophilization purposes.

What is claimed is:

1. A method of manufacturing a support media from a cross-linked polymerisate based on polymerised vinyl compounds and exhibiting residual vinyl groups, said method being characterised in that the polymerisate is subjected to a heating step under reduced access of oxygen.

2. The method of claim 1, characterised in that the polymerisate is surrounded by a liquid during the heat treatment.

3. The method of claim 1, characterised in that the polymerisate after the heat treatment is subjected to conditions reducing oxidised groups formed during the heat treatment.

4. The method of claim 1, characterised in that the polymerisate is a porous monolith, preferably having pore sizes in the interval 50 Å–50 μm.

5. The method of claim 1, characterised in that the polymerisate is in the form of non-porous or porous particles having sizes within the interval 1–500 μm, and, if pores are present, they are within the interval 50 Å–5000 Å.

6. The method of claim 1, characterised in that the polymerisate is in the form of beads/particles having a mean size within the interval 1–500 μm.

7. The method according to claim 1, characterised in that at least one or two of the vinyl compounds are vinyl hydrocarbons, for instance selected from vinyl styrenes that may be substituted with an alkyl group (for instance alkyl $(C_{1-26})$ or a functional group, and benzenes carrying at least two vinyl groups.

8. The method of claim 1, characterised in that the polymerisate is derivatized after the heat treatment, for instance hydrofilized, or equipped with groups allowing a certain type of chromatography, for instance one or more groups selected among affinity groups, such as ion exchange groups, hydrophobic groups, chelating groups, biospecific affinity groups, groups allowing π—π-interactions, groups allowing covalent chromatography etc.

9. The method of claim 1, characterised in that the polymerisate during the heating step is in contact with an organic compound comprising one or more functional groups reactive with the polymerisate under the conditions applied thereby enabling covalent binding of said organic compound to the polymerisate.

10. The method of claim 9, characterised in that the covalent binding of said organic compound introduces functionalities selected among amino groups, hydroxy groups, oxyethylene groups, ether groups, hydrocarbon groups.

11. The method of claim 6 wherein said beads/particles are monodisperse.

* * * * *